United States Patent
Park et al.

(10) Patent No.: US 9,982,032 B2
(45) Date of Patent: May 29, 2018

(54) STABLE LIQUID FORMULATION OF FUSION PROTEIN WITH IGG FC DOMAIN

(71) Applicant: Alteogen, Inc., Daejeon (KR)

(72) Inventors: Soon Jae Park, Daejeon (KR); Hye-Shin Chung, Daejeon (KR); Jin Hwan Kim, Daejeon (KR); Yong Mo Kim, Daejeon (KR); Jun Young Kim, Daejeon (KR)

(73) Assignee: ALTEOGEN, INC., Daejeon (KR)

( * ) Notice: Subject to any disclaimer, the term of this patent is extended or adjusted under 35 U.S.C. 154(b) by 0 days. days.

(21) Appl. No.: 15/190,378

(22) Filed: Jun. 23, 2016

(65) Prior Publication Data

US 2016/0376342 A1  Dec. 29, 2016

(30) Foreign Application Priority Data

Jun. 23, 2015  (KR) .................. 10-2015-0089186
Jun. 22, 2016  (KR) .................. 10-2016-0078234

(51) Int. Cl.

| | |
|---|---|
| C07K 14/71 | (2006.01) |
| A61K 38/18 | (2006.01) |
| A61K 9/08 | (2006.01) |
| A61K 47/26 | (2006.01) |
| A61K 38/17 | (2006.01) |
| A61K 9/00 | (2006.01) |
| A61K 47/18 | (2017.01) |

(52) U.S. Cl.
CPC ............ *C07K 14/71* (2013.01); *A61K 9/0019* (2013.01); *A61K 38/179* (2013.01); *A61K 47/183* (2013.01); *A61K 47/26* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 9,254,338 B2* | 2/2016 | Yancopoulos | A61K 38/179 |
| 9,416,167 B2* | 8/2016 | Dix | A61K 9/0019 |
| 9,631,030 B2* | 4/2017 | Hernandez Pascual | C07K 16/40 |
| 2015/0079087 A1 | 3/2015 | Dix | |
| 2015/0290325 A1* | 10/2015 | Kashi | C07K 14/7151 424/134.1 |
| 2016/0297877 A1* | 10/2016 | Sigl | A61K 39/00 |

FOREIGN PATENT DOCUMENTS

| | | |
|---|---|---|
| KR | 10-2012-0135387 A | 12/2012 |
| KR | 10-2015-0035681 A | 4/2015 |
| KR | 10-2015-0063305 A | 6/2015 |
| WO | WO 2006/044908 A2 | 4/2006 |
| WO | 2007-149334 A2 | 12/2007 |

OTHER PUBLICATIONS

DrugBank-Aflibercept-DrugBank—created May 24, 2013.*
Sumit Goswami et al., Developments and Challenges for mAb-Based Therapeutics, Antibodies 2013, vol. 2, p. 452-500.
Raafay Sophie et al., Aflibercept: a Potent Vascular Endothelial Growth Factor Antagonist for Neovascular Age-Related Macular Degeneration and Other Retinal Vascular Diseases, Biol Ther (2012) 2:3.
F Semeraro et al., Aflibercept in wet AMD: specific role and optimal use, Drug Design, Development and Therapy, Aug. 2013, 3(7), p. 711-722.
Min Kim, Intravitreal anti-vascular endothelial growth factor treatment for retinal diseases, J Korean Med Assoc Jul. 2014; 57(7), p. 614-623.
John A. Wells et al., Aflibercept, Bevacizumab, or Ranibizumab for Diabetic Macular Edema, The New England Journal of Medicine, Mar. 2015, 372;13, p. 1193-1203.

* cited by examiner

*Primary Examiner* — Elly-Gerald Stoica
(74) *Attorney, Agent, or Firm* — The PL Law Group, PLLC (57) ABSTRACT

A stable liquid formulation includes a fusion protein having an Fc domain of a human immunoglobulin G (IgG), in particular, a protein in which an Fc domain of a human immunoglobulin G (IgG) and a soluble extracellular domain of a vascular endothelial growth factor (VEGF) receptor are fused (e.g., aflibercept)). A composition for stabilizing a protein and a method for stabilizing a protein in which an Fc domain of an IgG and a soluble extracellular domain of a VEGF receptor are fused are disclosed. The present invention improves therapeutic effects on various ophthalmic diseases (e.g., retinal vein occlusion, diabetic macular edema, choroidal neovascularization and wet age-related macular degeneration, etc.) caused by abnormal angiogenesis, while pursuing stabilization of bioactivity through a stable liquid formulation suitable for intravitreal injection of an anti-VEGF-Fc fusion protein including aflibercept.

4 Claims, 6 Drawing Sheets

STABLE LIQUID FORMULATION OF FUSION PROTEIN WITH IGG FC DOMAIN

CROSS-REFERENCE TO RELATED APPLICATION

This application claims priority to and the benefit of Korean Patent Application No. 10-2015-0089186, filed on Jun. 23, 2015, and Korean Patent Application No. 10-2016-0078234, filed on Jun. 22, 2016, the disclosures of which are incorporated herein by reference in its entirety.

BACKGROUND

1. Field of the Invention

The present invention relates to a stable liquid formulation of a fusion protein having an Fc domain of a human immunoglobulin G (IgG). More particularly, the present invention relates to a liquid formulation having a stabilized protein in which an Fc domain of a human IgG and a soluble extracellular domain of a vascular endothelial growth factor (VEGF) receptor are fused, for example, aflibercept, to a composition for stabilizing a protein in which an Fc domain of an IgG and a soluble extracellular domain of a VEGF receptor are fused, and to a method for stabilizing a protein in which an Fc domain of an IgG and a soluble extracellular domain of a VEGF receptor are fused.

2. Discussion of Related Art

A type of cell-inducing dimer mitogen having selectivity to vascular endothelial cells has been identified, and is designated as vascular endothelial growth factor (VEGF). The VEGF is an important factor which increases angiogenesis and vascular permeability.

It has been known that the VEGF activates VEGF receptors (i.e., VEGFR-1, VEGFR-2, and VEGFR-3) which are membrane-spanning tyrosine kinase receptors. Among the VEGF receptors, VEGFR-1 and VEGFR-2 have 7 Ig-like sequences, a single transmembrane region, and a consensus tyrosine kinase region in the extracellular domain in order to bind to the VEGF. These features are applied as a sequence for an anti-VEGF agent. Aflibercept, which is an ophthalmic therapeutic agent, is a soluble decoy receptor of about 115 kDa (including glycosylation) having a structure in which a second binding domain of VEGFR-1 and a third binding domain of VEGFR-2 are fused with an Fc region of a human IgG1 (see [Drug Design Development and Therapy (2013), 3(7), 711-722]).

In mechanisms via the VEGF, abnormal angiogenesis is associated with ophthalmic diseases such as wet age-related macular degeneration, diabetic macular edema, and macular edema in retinal vein occlusion, etc. (see [J. Korean Med. Assoc. (2014), 57(7), 614-623]).

Examples of therapeutic agents for these ophthalmic diseases include pegaptanib (trade name: Macugen), ranibizumab (trade name: Lucentis), bevacizumab (trade name: Avastin), and aflibercept (trade name: Eylea). Aflibercept is approved for the treatment of wet age-related macular degeneration in 2011 (see [Biol. Ther. (2012), 2(3) 1-22], and [Drug Design Development and Therapy (2013), 3(7), 711-722], etc.). Among the therapeutic agents above, aflibercept has been reported to have the best therapeutic effect on patients with diabetic macular edema having advanced amblyopia (see [NEJM (2015), 372(13) 1193-1203]. Aflibercept has been commercialized as a therapeutic agent for metastatic colorectal cancers (trade name: Zaltrap) and a therapeutic agent for retinal vein occlusion, diabetic macular edema, choroidal neovascularization, and wet age-related macular degeneration (trade name: Eylea).

Physicochemical modifications occur in protein drugs including antibody drugs under the non-optimal condition. In particular, factors such as temperature, pH, concentration of a salt, contact with air, concentration of a protein, and types of buffers significantly affect oxidation, deamidation, isomerization, and polymerization, of a protein. These modifications cause aggregation, and generate fragments, isomers of the protein, so that bioactivity may be reduced. These properties differ among proteins. Particularly, for an Fc fusion protein, due to the problem in folding, separate 3 peaks appear in hydrophobic interaction chromatography (see [Antibodies (2013), 2,452-500]).

International Publication WO 2007/149334 discloses "an ophthalmic formulation including 1-100 mg/ml of aflibercept, 0.01-5% of an organic cosolvent (e.g., polysorbate, polyethylene glycol, propylene glycol, etc.), 30-150 mM of an isotonic agent (e.g., NaCl, KCl etc.), 5-40 mM of sodium phosphate buffer and 1.0-7.5% of stabilizer (e.g., sucrose, sorbitol, glycerol, trehalose, and mannitol, etc.)" and "a lyophilizable formulation including 5-50 mg/ml of aflibercept, 5-25 mM of sodium phosphate buffer, 0.01-0.15% of an organic cosolvent, 1-10% of a stabilizer, and 20-150 mM of an isotonic agent." The formulation disclosed in International Publication WO 2007/149334 may be applied to a prefilled syringe suitable for intravitreal administration.

For the ophthalmic formulation and lyophilizable formulation disclosed in International Publication WO 2007/149334, an effect of inhibiting production of impurities and byproducts due to aggregation, fragmentation and isomerization of aflibercept, was reported. However, the formulation in International Publication WO 2007/149334 was problematic in that the effect of stabilizing aflibercept was markedly reduced under harsh conditions such as high temperature condition of 40° C. or more, or shaking condition.

Therefore, the present inventors have completed the present invention by developing a liquid formulation having enhanced stability under the harsh conditions as well as stably maintaining a fusion protein having an IgG Fc domain such as aflibercept under the storing condition for a long period of time.

SUMMARY OF THE INVENTION

The present invention is derived to solve the problems described above, and provides a formulation having stabilized protein in which an Fc domain of a human immunoglobulin G (IgG) and a soluble extracellular domain of a vascular endothelial growth factor (VEGF) receptor are fused.

Another aspect of the present invention is to provide a composition for stabilizing a protein in which an Fc domain of an IgG and a soluble extracellular domain of a VEGF receptor are fused.

Still another aspect of the present invention is to provide a liquid formulation including the composition for stabilizing a protein in which an Fc domain of an IgG and a soluble extracellular domain of a VEGF receptor are fused; and aflibercept.

The present invention provides a liquid formulation, including: a protein in which a soluble extracellular domain of a vascular endothelial growth factor (VEGF) receptor and an Fc domain of a human immunoglobulin G (IgG) are fused; and a buffer including a histidine salt and having pH ranging from 5.7 to 6.2.

According to a preferred embodiment of the present invention, the soluble extracellular domain of the VEGF receptor may include immunoglobulin-like domain 2 of a first VEGF receptor and immunoglobulin-like domain 3 of a second VEGF receptor.

According to another preferred embodiment of the present invention, the fusion protein may be present in an amount of 10 to 40 mg/ml.

According to still another preferred embodiment of the present invention, the histidine salt may be histidine-HCl or histidine-acetate.

According to another preferred embodiment of the present invention, wherein the concentration of the histidine salt may be 10 mM to 50 mM.

According to still another preferred embodiment of the present invention, the liquid formulation may further include one or more stabilizers selected from the group consisting of sugars and surfactants.

According to another preferred embodiment of the present invention, the sugar may be at least one selected from the group consisting of 2.5% to 10% of sucrose, trehalose, mannitol, and glucose.

According to still another preferred embodiment of the present invention, the sugar may be 5% to 10% of sucrose.

According to another preferred embodiment of the present invention, the surfactant may be 0% to 0.03% of polysorbate 20 or polysorbate 80, for example, 0% or 0.01% to 0.03%.

Further, the present invention provides a composition for stabilizing a protein in which a soluble extracellular domain of a VEGF receptor and an Fc domain of an IgG are fused, the composition including: a buffer including a histidine salt and having pH ranging from 5.7 to 6.2; and one or more stabilizers selected from the group consisting of sugars and surfactants, wherein, the histidine salt is 10 mM to 50 mM of histidine-HCl or histidine-acetate; the sugar is at least one selected from the group consisting of 2.5% to 10% of sucrose, trehalose, mannitol and glucose; and the surfactant is 0% to 0.03% of polysorbate 20 or polysorbate 80, for example, 0% or 0.01% to 0.03%.

Also, the present invention provides a method for stabilizing a protein in which an Fc domain of a human immunoglobulin G (IgG) and a soluble extracellular domain of a vascular endothelial growth factor (VEGF) receptor are fused by using a buffer including a histidine salt and having pH ranging from 5.7 and 6.2.

According to a preferred embodiment of the present invention, the buffer may further include one or more stabilizers selected from the group consisting of sugars and surfactants.

Further, the present invention provides a liquid formulation including a buffer including a histidine salt and having pH ranging from 5.7 to 6.2; one or more stabilizers selected from the group consisting of sugars and surfactants; and aflibercept; wherein the histidine salt is 10 mM to 50 mM of histidine-HCl or histidine-acetate, and the sugar is at least one selected from the group consisting of 2.5% to 10% of sucrose, trehalose, mannitol and glucose, and the surfactant is 0% to 0.03% of polysorbate 20 or polysorbate 80, for example, 0% or 0.01% to 0.03%.

According to a preferred embodiment of the present invention, the liquid formulation may be suitable for intravitreal injection.

In the liquid formulation provided by the present invention, production of impurities and byproducts due to aggregation, fragmentation and isomerization of the fusion protein having an Fc domain of a human immunoglobulin G (IgG) (in particular, the protein in which an Fc domain of a human immunoglobulin G (IgG) and a soluble extracellular domain of a vascular endothelial growth factor (VEGF) receptor are fused (e.g., aflibercept)) under harsh conditions such as a high temperature condition of 40° C. or more or shaking condition, as well as general storing condition, is significantly reduced, and thus stability for long-term storage may be enhanced.

Also, the present invention improves therapeutic effects on various ophthalmic diseases (e.g., retinal vein occlusion, diabetic macular edema, choroidal neovascularization and wet age-related macular degeneration, etc.) caused by abnormal angiogenesis, while pursuing stabilization of bioactivity through a stable liquid formulation suitable for intravitreal injection of an anti-VEGF-Fc fusion protein including aflibercept.

BRIEF DESCRIPTION OF THE DRAWINGS

The above and other aspects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, the present invention will be described in more detail.

As described above, the previously provided formulation in which a fusion protein such as aflibercept having an IgG Fc domain is stabilized has a problem in that stability is significantly reduced under the harsh conditions, so that it has been required to develop a formulation capable of maintaining the fusion protein under the harsh conditions in addition to the general storing conditions.

Therefore, the present invention has found a solution for above-described problems by providing a liquid formulation including: a protein in which an Fc domain of a human immunoglobulin G (IgG) and a soluble extracellular domain of a vascular endothelial growth factor (VEGF) receptor are fused; and a buffer including a histidine salt and pH ranging from 5.7 to 6.2. Since the liquid formulation of the present invention stably maintains the fusion protein under general storing conditions for a long period of time and also significantly reduces production of impurities and byproducts under harsh conditions, it is possible to provide a formulation having significantly improved stability relative to the known fusion protein formulation under the inevitable condition where the optimal storing condition would not be provided.

The present invention provides a liquid formulation including a protein in which an Fc domain of a human immunoglobulin G (IgG) and a soluble extracellular domain of a vascular endothelial growth factor (VEGF) are fused; and a buffer including a histidine salt and having a pH ranging from 5.7 to 6.2.

In the fusion protein, which is an active ingredient of the liquid formulation, the soluble extracellular domain of the VEGF may include immunoglobulin-like domain 2 of a first VEGF receptor and immunoglobulin-like domain 3 of a second VEGF receptor, and the Fc domain of a human immunoglobulin G (IgG) may be an Fc domain of IgG1, IgG2, IgG3 or IgG4, preferably an Fc domain of IgG1. The Fc region includes hinge-CH1-CH2-CH3, and CH1 may be deleted.

In the liquid formulation of the present invention, the fusion protein may be included in an amount of about 10-100 mg/ml, preferably about 10-80 mg/ml, and more preferably about 10-40 mg/ml.

In the liquid formulation according to the present invention, the "buffer" refers to a buffered solution enduring changes in pH due to the action of an acid-base conjugate ingredient of the buffer. In an embodiment of the present invention, a buffer including a histidine salt and having pH ranging from 5.7 to 6.2 was used, wherein the histidine salt is preferably histidine-HCl or histidine-acetate, and the histidine salt concentration may be 10 mM to 50 mM.

Figure 1:
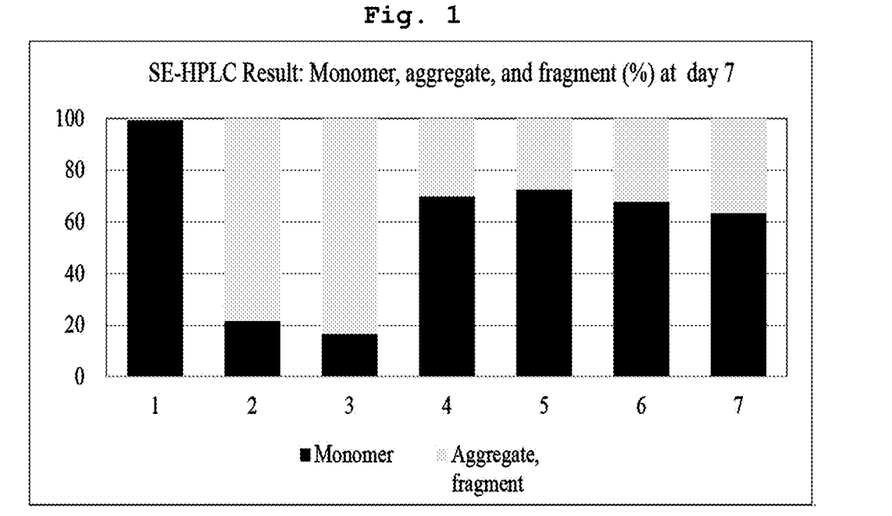
FIG. 1 is a graph measuring changes in fragment and aggregate contents of a sample stored for 7 days at 40° C. by varying pH of the histidine salt buffer including aflibercept.
Figure 2:
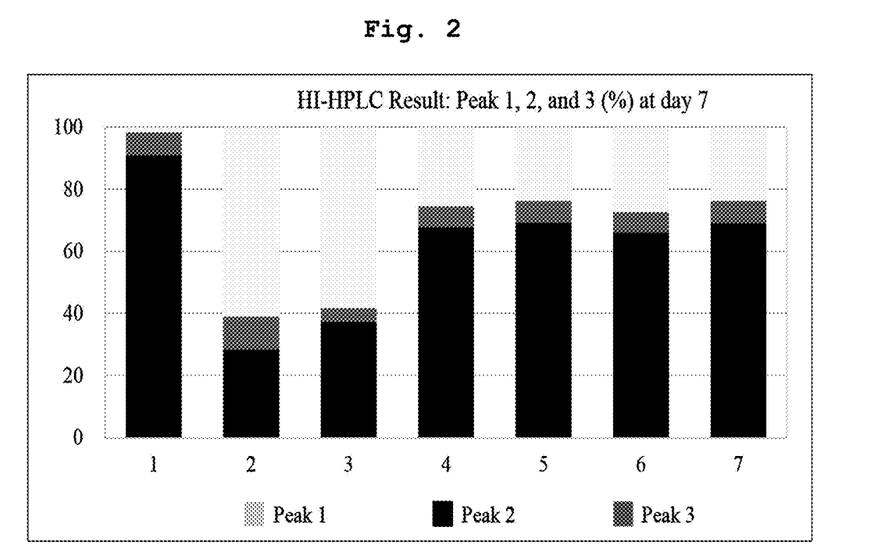
FIG. 2 is a graph measuring changes in peaks 1, 2, and 3 contents (%) in hydrophobic interaction high-performance liquid chromatography (HI-HPLC) of a sample stored for 7 days at 40° C. by varying pH of the histidine salt buffer including aflibercept.

As shown in FIGS. 1 and 2, for the formulation using the histidine salt buffer having pH of 5.7 to 6.2, the effect of inhibiting production of fragments and aggregates was significantly increased than that of control formulation (2). In particular, stability of the formulation at pH 6.0 is most excellent.

When pH of the buffer was decreased to less than 5.7, as shown in FIGS. 1 and 2, stability of the formulation was significantly reduced. For pH of above 6.5, a problem of increasing impurities caused by disruption or aggregation of a target protein may occur.

Figure 3A:
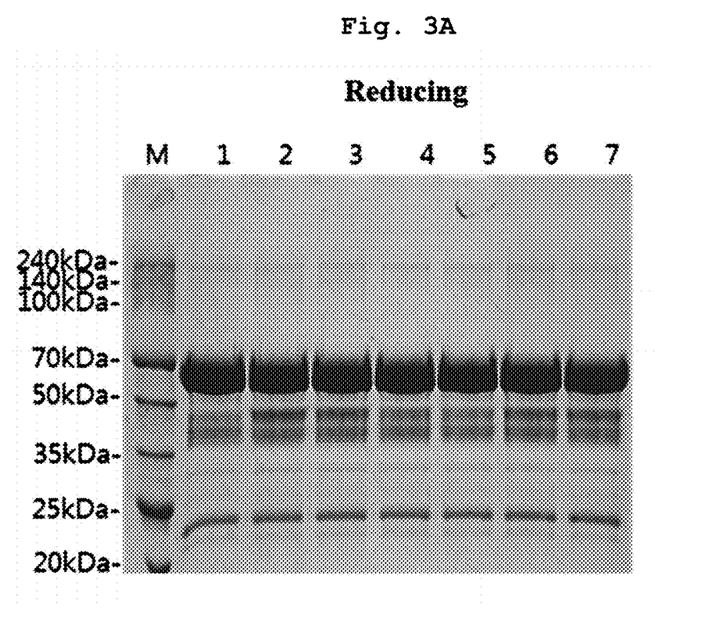
FIGS. 3A and 3B show SDS-PAGE analysis results of various buffers (sodium phosphate, succinate, histidine-HCl, histidine-acetate, and sodium acetate) including aflibercept after being stored for 21 days at 40° C.
Figure 3B:
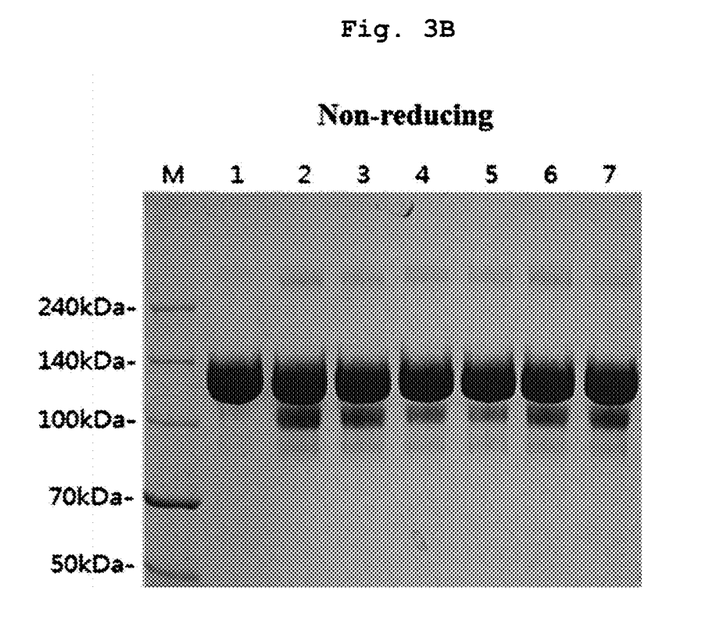

In addition, as shown in FIGS. 3A and 3B, it has been found that the effect of inhibiting production of impurities and aggregates is most excellent, when the histidine-HCl or histidine-acetate buffer was used among various buffer conditions.

Figure 5:
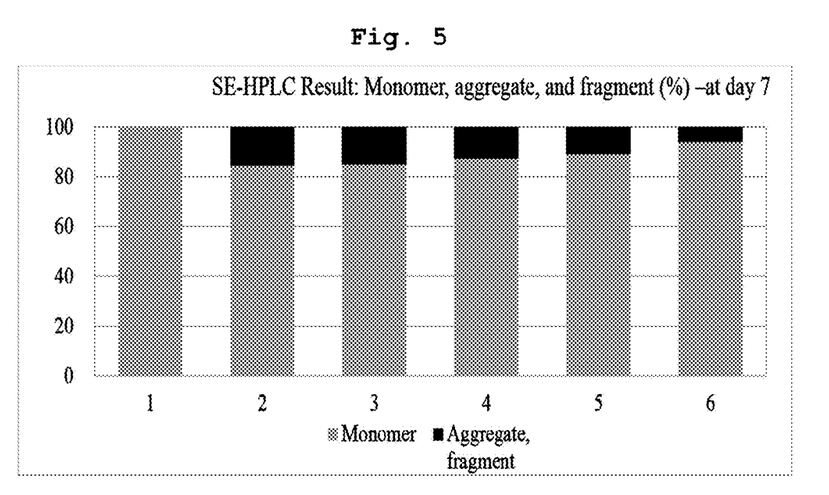
FIG. 5 is a graph measuring changes in fragment and aggregate contents (%) of a sample stored for 7 days at 45° C. by varying sucrose concentrations in the histidine salt buffer including aflibercept.

Further, the formulation (3) of FIG. 5 was to measure stability of aflibercept in the 10 mM histidine salt buffer having pH 6.0, and it has been found that aflibercept stability similar to that of control formulation (2) was maintained under the buffer condition.

The liquid formulation of the present invention may further include one or more stabilizer selected from the group consisting of sugars and surfactants in addition to the fusion protein, which is an active ingredient of the liquid formulation, and the histidine salt buffer.

In the liquid formulation of the present invention, the sugar is any one selected from the group consisting of trehalose, sucrose, mannitol, sorbitol, glucose, lactose, xylitol, inositol, glycerol and hydroxypropyl cyclodextrin, and preferably any one selected from the group consisting of trehalose, sucrose, mannitol and glucose. The sugar concentration may be 2.5-10% (v/v).

Figure 4A:
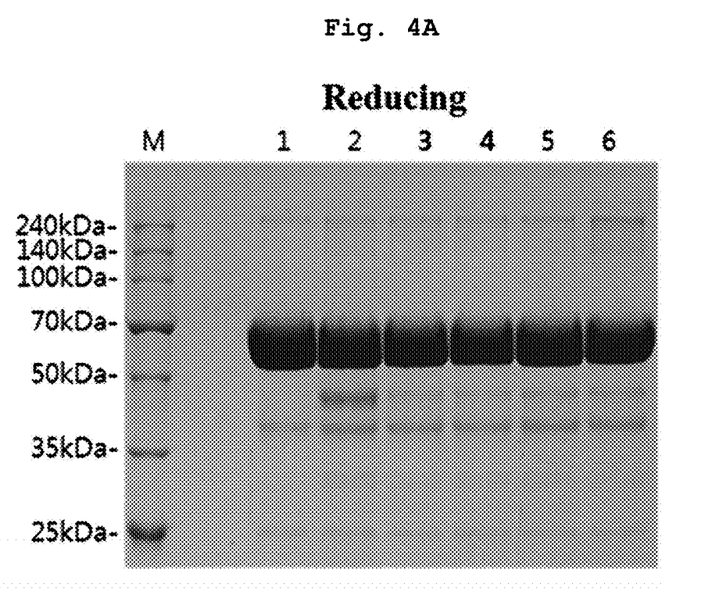
FIGS. 4A and 4B show SDS-PAGE analysis results of a formulation including various sugars (trehalose, sucrose, mannitol, and glucose) in the histidine salt buffer including aflibercept after being stored for 8 days at 50° C.
Figure 4B:
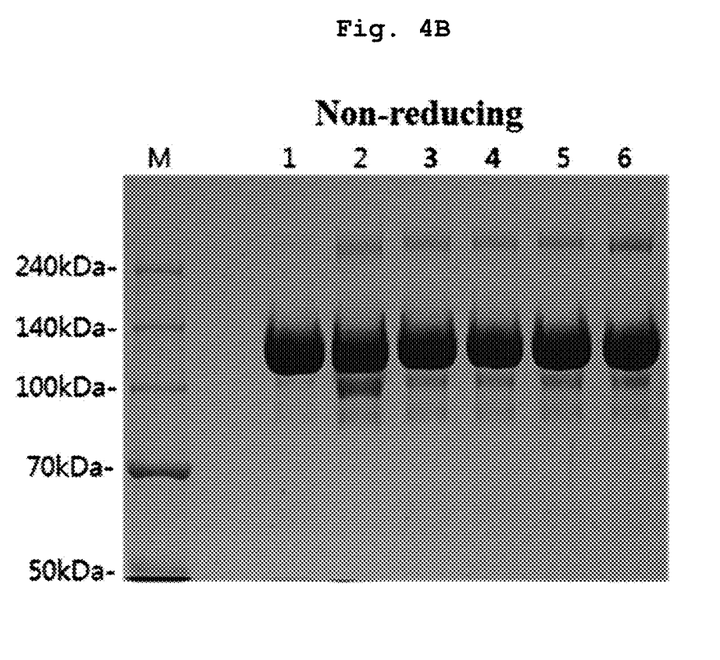

As shown in FIGS. 4A and 4B, all of formulations (3) to (6) which respectively include trehalose, sucrose, mannitol, and glucose in the histidine salt buffer showed enhanced aflibercept stability than the control formulation (2). In particular, in the case where the sugar was sucrose, aflibercept stability was most excellent.

Further, as shown in FIG. 5, formulation (3) without sucrose showed similar formation stability as that of control formulation (2). As sucrose concentration increased, the effect of inhibiting production of aggregates and impurities increased with respect to control (2).

In the liquid formulation of the present invention, the surfactant may be used to ophthalmic drug delivery. The types of the surfactants are not limited, and include anionic surfactants, cationic surfactants, non-ionic surfactants, and zwitter-ionic surfactants, etc. The surfactant concentration may be about 0-0.3% (v/v), for example, 0% or 0.01% to 0.03%.

Examples of the anionic surfactant may include sulfate, sulfonate, phosphate, and carboxylate, but not limited thereto.

Examples of the cationic surfactant may include octenidine dihydrochloride, cetyl trimethylammonium bromide (CTAB), hexadecyl trimethylammonium bromide, cetyl trimethylammonium chloride (CTAC), cetyl pyridinium chloride (CPC), benzalkonium chloride (BAC), benzethonium chloride, 5-bromo-5-nitro-1,3-dioxane, dimethyldioctadecylammonium chloride, cetrimonium bromide, dioctadecyldimethylammonium bromide (DODAB), etc.

Examples of the non-ionic surfactant may include polyoxyethylene glycol alkyl ether, polyoxypropylene glycol alkyl ether, polyoxyethylene glycol ocylphenol ether (e.g. Triton X-100, etc.), polyoxyethylene glycol alkylphenol ether, glycerol alkyl ester, polyoxyethylene glycol sorbitan alkyl ester (e.g. polysorbate 20, polysorbate 80, etc.), cocamide MEA, cocamide DEA, dodecyldimethylamine oxide, copolymer of polyethylene glycol and polypropylene glycol, polyethoxylated tallow amine (POEA), etc.

Examples of the zwitter-ionic surfactant may include CHAPS(3-[(3-cocamidopropyl)dimethylamomonio]-1-propane sulfate), cocamidopropyl hydroxysultaine, etc.

Moreover, as surfactants, alkyl sulfates such as ammonium lauryl sulfate, sodium lauryl sulfate (SLS), sodium dodecyl sulfate (SDS), sodium lauryl ether sulfate (SLES), sodium myreth sulfate; docusates such as dioctyl sodium sulfosuccinate, perfluorooctane sulfonate (PFOS), perfluorobutane sulfonate, linear alkylbenzene sulfonate (LAB); phospholipids such as phosphatidylserine, phosphatidylethanolamine, phosphatidylcholine; and sphingomyelines.

Figure 6:
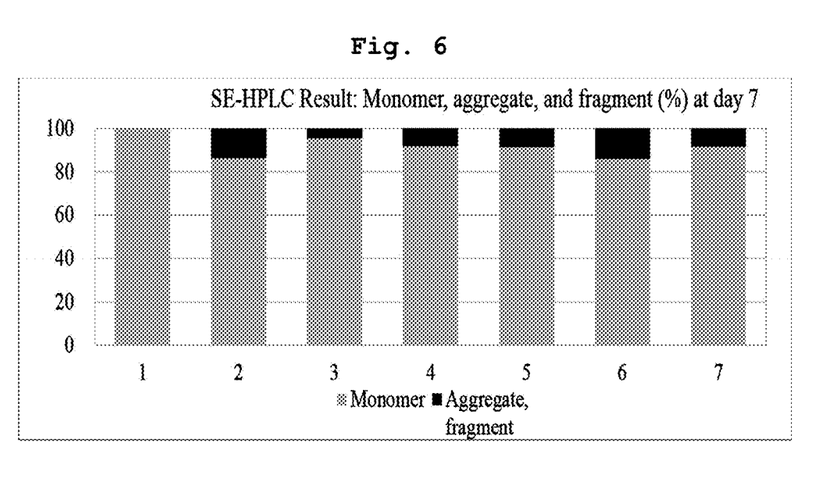
FIG. 6 is a graph measuring changes in fragment and aggregate contents (%) of a sample stored for 7 days at 45° C., wherein the sample is a formulation including various salts (sodium chloride, ammonium chloride, ammonium sulfate, and potassium chloride) in the histidine salt buffer including aflibercept.

In an embodiment of the present invention, to evaluate stability of formulations depending whether an additional salt ingredient besides components included in the liquid formulation described above is added or not, formulations respectively including various salts and a formulation without salt were prepared. Consequently, as shown in FIG. 6, it has been observed that the effect of inhibiting production of impurities and aggregates was most excellent in the formulation without additional salt ingredients.

The liquid formulation according to the present invention maintains stability of the fusion protein under general storing conditions for a long period of time and has an excellent effect of inhibiting production of impurities and byproducts of the fusion protein under harsh conditions, and thus stability of the fusion protein is enhanced than that of the typical liquid formulation. Herein, the term "harsh conditions" refers to an environment chemically and physically unfavorable to the fusion protein, and leads to unacceptable protein stability. The harsh conditions include, for example, high temperature or shaking condition.

Herein, the term "stable" indicates that a protein essentially maintains physical and/or chemical stability and/or biological activity thereof during storing. Various analytical techniques for measuring protein stability are available in the art. Stability may be measured at selected temperature and selected period.

The protein may be considered to "maintain physical stability thereof" in a formulation, when the protein shows less or no change in aggregation, precipitation, and/or modification during observation of color and/or transparency with naked eyes, UV light-scattering measurement (i.e., notable aggregates are measured), or size exclusion chromatograph (SED) measurement.

As shown in FIGS. 1 to 6 and 8, the various conditions of liquid formulations of the present invention showed significantly inhibited production of impurities and aggregates than control formulation (2), thereby being relatively stable for 7 to 21 days at a temperature ranging from 40 to 50° C.

Figure 7A:
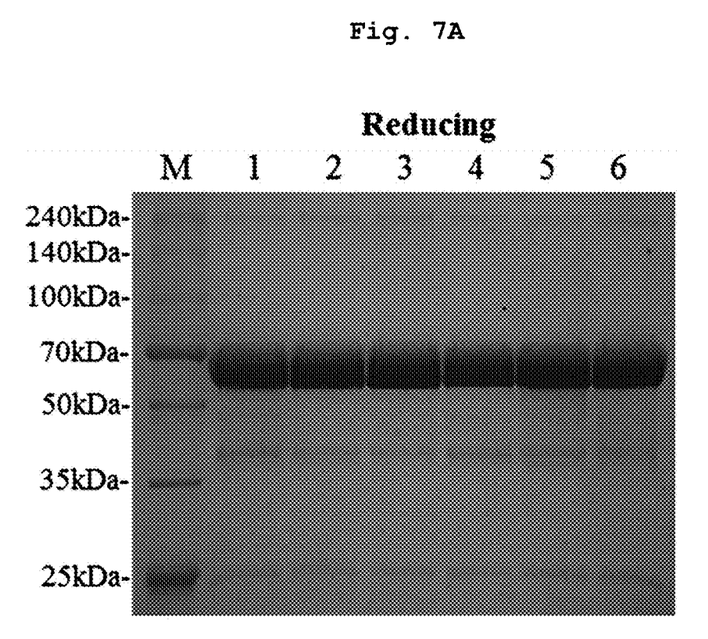
FIGS. 7A and 7B show SDS-PAGE results of a formulation including the histidine salt buffer including aflibercept with or without polysorbate, wherein the formulation is stored for 7 days at 25° C. with shaking at 200 rpm.
Figure 7B:
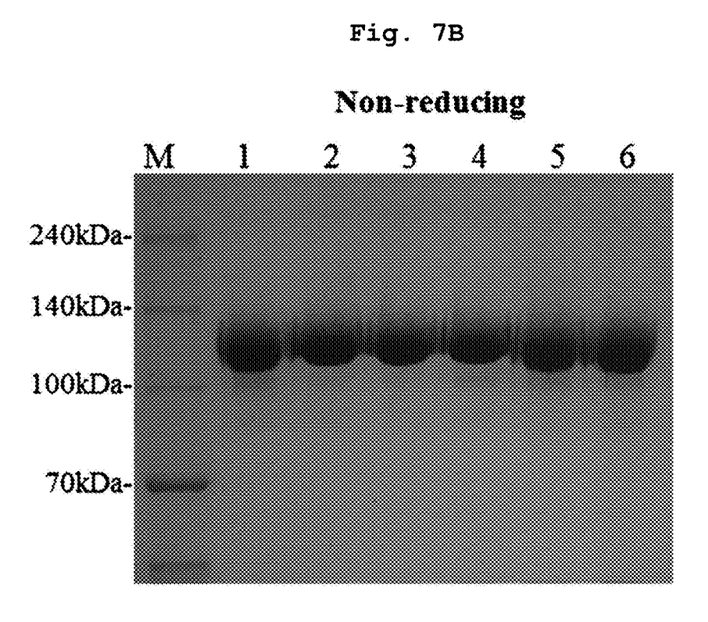

Various conditions of liquid formulations of the present invention were stored at 25° C. with shaking at 200 rpm for 7 days, and then each formulation was subjected to SE-HPLC and HI-HPLC. Consequently, irrespective of presence and absence of polysorbate 20, production of aggregates and modifications was inhibited. Likewise, in the SDS-PAGE (non-reducing) (FIG. 7) and SE-HPLC results, it has been observed that production of aggregate and protein fragments was inhibited than that of control (1) irrespective of presence and absence of polysorbate under the shaking condition at 25° C. for 7 days. In particular, the effect of inhibiting production of aggregates and protein fragments was slightly better for the formulation without polysorbate.

The present invention provides a method of stabilizing a protein in which an Fc domain of a human immunoglobulin G (IgG) and a soluble extracellular domain of a vascular endothelial growth factor VEGF receptor are fused by using a buffer including a histidine salt and having pH of 5.7 to 6.2.

Since he description about feature of the buffer and fusion protein is the same as described above, overlapping contents are not described in order to avoid excess complicity of the present specification.

In the method of stabilizing the fusion protein of the present invention, the buffer may further include one or more stabilizers selected from the group consisting of sugars and surfactants.

Since description about additionally added sugar and surfactant are the same as described above, these features are not described.

The present invention also provides a composition for stabilizing a fusion protein in which an Fc domain of an IgG and a soluble extracellular domain of a VEGF receptor are fused, the composition including a buffer including a histidine salt and having pH of 5.7 to 6.2; and one or more stabilizers selected from the group consisting of sugars and surfactants, wherein the histidine salt is 10 mM to 50 mM histidine-HCl, or histidine-acetate; the sugar is any one selected from the group consisting of 2.5% to 10% of sucrose, trehalose, mannitol, and glucose; and the surfactant is any one selected from 0% to 0.03%, of polysorbate 20 or polysorbate 80, for example, 0% or 0.01% to 0.03%.

The description about features of the stabilizing composition is the same as described above, and thus overlapping contents are not described in order to avoid excess complicity of the present specification.

The present invention also provides a liquid formulation including the composition for stabilizing a protein in which an Fc domain of an IgG and a soluble extracellular domain of a VEGF receptor are fused; and aflibercept.

The liquid formulation may be used for medicinal use for preventing or treating various diseases without limitation as long as the diseases can be treated with aflibercept treatment. Preferably, the formulation may be used to treat or prevent various ophthalmic diseases such as retinal vein occlusion, diabetic macular edema, choroidal neovascularization and wet age-related macular degeneration, etc.

The liquid formulation according to the present invention may further include a pharmaceutically acceptable carrier, diluent, and excipient, etc.

The pharmaceutically acceptable carrier is a typically used in a formulation, and may include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate and mineral oil, but not limited thereto.

In addition to above ingredients, the liquid formulation of the present invention may further include lubricants, wetting agents, sweetening agents, flavoring agents, emulsifiers, suspensions, preservants, etc. The suitable pharmaceutically acceptable carrier and formulation are described in detail in Remington's Pharmaceutical Sciences (19th ed., 1995).

The liquid formulation of the present invention may be administered in various routes depending on purposes. The formulation is preferably administered through intravitreal injection for the treatment of ophthalmic diseases. Also, the formulation may be applied to a pre-filled syringe suitable for intravitreal injection.

The suitable amount of administration of the liquid formulation of the present invention may vary depending on factors such as formulation methods, administration modes, age, weight, sex, and disease state of patients, foods, administration time, administration routes, excretion rates, and reaction sensitivity. Doctors with ordinary skills may easily determine and prescribe the amount of administration effective for desired therapy or prevention.

It should be understood that the scope of the present invention is not limited to the following examples, and all technical and scientific terms used in the specification have the same meaning as those typically appreciated by a person with ordinary skill in the technical field to which the present invention belongs ("a person skilled in the art").

EXAMPLES

Example 1

Evaluation of Optimal pH Condition for Formulation

In Example 1 and following Examples 2 to 5, the liquid formulation disclosed in prior art document International Publication WO 2007/149334 was stored at 5±3° C., and used as control (1). Also, control (1) was subjected to the harsh condition (a temperature of 40° C. or more) and used as control (2). Then, stability of the formulation was compared to stability of various forms of liquid formulations of the present invention.

In the present example, to identify the optimal pH of the liquid formulation containing, as an active ingredient, aflibercept which is an anti-VEGF-Fc fusion protein, samples were prepared for each pH based on the histidine salt buffer as follows.

Specifically, the final aflibercept concentration was adjusted to 40 mg/ml, and (1) a formulation having 10 mM sodium phosphate, pH 6.2, 5% sucrose, 40 mM NaCl, 0.03% polysorbate 20 (formulation stored at 5±3° C.); (2) a formulation having 10 mM sodium phosphate, pH 6.2, 5% sucrose, 40 mM NaCl, 0.03% polysorbate 20 (formulation stored at 40° C.) and formulations having 10% trehalose, 0.01% (w/v) polysorbate 20 and 10 mM histidine-HCl buffer respectively having pH of (3) 5.5; (4) 5.7; (5) 6.0; (6) 6.2; and (7) 6.5 were stored at 40° C. for 7 days. Then, impurities produced with lapse of time were analyzed through size exclusion high-performance liquid chromatography (SE-HPLC) and HI-HPLC.

In SE-HPLC analysis, TSK-gel G3000SWXL (7.8×300 mm) column (TOSOH Co., Japan) was used, and 0.2 M potassium phosphate (pH 6.2), 0.25 M KCl and 0.05% (w/v) $NaN_3$ buffer were used at a flow rate of 0.5 ml/min. The peak of the anti-VEGF-Fc fusion protein was analyzed at an absorbance of 280 nm.

In SE-HPLC analysis for the sample stored at 40° C. for 7 days, the monomer content was calculated, and aggregates, which are high molecular weight impurities, and fragments, which are low molecular weight impurities, were combined and calculated. FIG. 1 showed SE-HPLC result on day 7. It is indicated that, when comparing with control (2), the formulation of the present invention shows significantly reduced production of aggregates and fragments at pH 5.7, 6.0, 6.2 and 6.5, and thus the formulation is stable. Also, among various pH conditions, it has been identified that stability of the formulation was highest at pH 6.0.

In HI-HPLC analysis, TSK Phenyl-5PW (7.5×300 mm) column was used. As a mobile phase, 50 mM sodium phosphate (pH 7.0) was used. 2 M NaCl, 50 mM sodium phosphate (pH 7.0) and 30% (v/v) acetonitrile buffer was used and allowed to flow at a concentration gradient of 0%-90%. Then, the peak of the anti-VEGF-Fc fusion protein was analyzed at an absorbance of 220 nm. During the HI-HPLC analysis, three main peaks, i.e. peak 1, peak 2 and peak 3 appeared. When changes in the peak were less, it was considered as stable.

FIG. 2 shows a result of HI-HPLC analysis of the sample stored at 40° C. with lapse of time. FIG. 2 showed changes in peak 1, peak 2, and peak 3 under each condition, and it has been found that, when comparing to control (2), the formulation of the present invention under the pH 5.7, 6.0, 6.2 and 6.5 conditions showed significantly less changes in peaks. Also, among various other pH conditions, the formulation was most stable at pH 6.0 condition, relatively.

Example 2

Evaluation of Optimal Buffer Condition for Formulation

In the present example, to identify the optimal buffer condition for the liquid formulation containing, as an active ingredient, aflibercept which is an anti-VEGF-Fc fusion protein, samples were prepared as follows.

Specifically, the final aflibercept concentration was adjusted to 40 mg/ml, and (1) a formulation having 10 mM sodium phosphate, pH 6.2, 5% sucrose, 40 mM NaCl, 0.03% polysorbate 20 (formulation stored at 5±3° C.); (2) a formulation having 10 mM sodium phosphate, pH 6.2, 5% sucrose, 40 mM NaCl, 0.03% polysorbate 20 (formulation stored at 40° C.), and various formulation respectively including 0.01% polysorbate 20 and 2.5% sucrose in a buffer of (3) 10 mM sodium phosphate, pH 6.0; (4) 10 mM histidine-HCl, pH 6.0; (5) 10 mM histidine-acetate, pH 6.0; (6) 10 mM succinate, pH 6.0; and (7) 10 mM sodium acetate, pH 5.6 were stored at 40° C. for 21 days. Then, same as example 1, a monomer, aggregates, and variants were analyzed with lapse of time through SE-HPLC and HI-HPLC.

Thereafter, SDS-PAGE analysis was performed. To 20.0 ul of analytic sample diluted to 1 mg/ml, 5.0 ul of 5× sample buffer (reducing or non-reducing) was added, and the resultant was reacted at 100° C. for 5 minutes and used for analysis. 12.5 ul of the final analytic sample was loaded per well. As a marker (M), DokDo-Mark™ protein marker was used, and loaded at 3 ul per well. 10% SDS-PAGE (reducing), and 6% SDS-PAGE (non-reducing) gel electrophoresis were performed. Then, staining was performed with coomassie blue. Until clear bands appear, destaining was performed.

As a result of SDS-PAGE (non-reducing) (FIG. 3B), and SE-HPLC and HI-HPLC analysis, it has been found that, when comparing to control (2), the formulations of 10 mM histidine-HCl and 10 mM histidine-acetate of the present invention significantly inhibited production of aggregates and impurities.

Example 3

Evaluation of Optimal Sugar Condition for Formulation

In the present example, to identify the optimal sugar for the liquid formulation containing, as an active ingredient, aflibercept which is an anti-VEGF-Fc fusion protein, samples were prepared as follows.

Specifically, the final aflibercept concentration was adjusted to 40 mg/ml, and (1) a formulation having 10 mM sodium phosphate, pH 6.2, 5% sucrose, 40 mM NaCl, 0.03% polysorbate 20 (formulation stored at 5±3° C.); (2) a formulation having 10 mM sodium phosphate, pH 6.2, 5% sucrose, 40 mM NaCl, 0.03% polysorbate 20 (formulation stored at 50° C.), and formulations respectively including, in 10 mM histidine-acetate buffer (pH 6.0) with 0.01% polysorbate 20, (3) 2.5% trehalose; (4) 2.5% sucrose; (5) 2.5% mannitol; and (6) 2.5% glucose were stored at 50° C. for 8 days. Then, same as Examples 1 and 2, monomers, aggregates, and variants produced with lapse of time were analyzed through SDS-PAGE (reducing, non-reducing), SE-HPLC, and HI-HPLC.

As a result of SDS-PAGE (reducing, non-reducing) analysis (FIGS. 4A and 4B) and SE-HPLC and HI-HPLC analysis, when comparing to control (2), all formulations respectively including trehalose, sucrose, mannitol, and glucose of the present invention significantly inhibited production of aggregates and impurities. In particular, the effect of inhibiting production of impurities and aggregates was most excellent in the formulation including sucrose.

Example 4

Evaluation of Optimal Sugar Concentration for Formulation

In the present example, to identify the optimal sugar concentration for the liquid formulation containing, as an active ingredient, aflibercept which is an anti-VEGF-Fc fusion protein, samples were prepared as follows.

Specifically, the final aflibercept concentration was adjusted to 40 mg/ml, and (1) a formulation having 10 mM sodium phosphate, pH 6.2, 5% sucrose, 40 mM NaCl, 0.03% polysorbate 20 (formulation stored at 5±3° C.); (2) a formulation having 10 mM sodium phosphate, pH 6.2, 5% sucrose, 40 mM NaCl, 0.03% polysorbate 20 (formulation stored at 45° C.), and formulations respectively having, in 10 mM histidine-acetate buffer (pH 6.0) with 0.01% polysorbate 20, sucrose of varying concentrations of (3) 0%; (4) 2.5%; (5) 5%; and (6) 10% were stored at 45° C. for 7 days. Then, same as Examples 1 and 2, monomers, aggregates, and variants produced with lapse of time were analyzed through SDS-PAGE (reducing, non-reducing), SE-HPLC, and HI-HPLC.

In the SE-HPLC analysis results, it has been found that the formulation without sucrose of the present invention (3) showed formulation stability similar to that of control (2), and as the sucrose concentration in each formulation of the present invention increased, the effect of inhibiting production of aggregates and impurities was increased with respect to control (2) (FIG. 5).

Example 5

Evaluation of Additional Salt Condition

In the present example, to identify an additional salt ingredient optimal for the liquid formulation containing, as an active ingredient, aflibercept which is an anti-VEGF-Fc fusion protein, samples were prepared as follows.

Specifically, the final aflibercept concentration was adjusted to 40 mg/ml, and (1) a formulation having 10 mM sodium phosphate, pH 6.2, 5% sucrose, 40 mM NaCl, 0.03% polysorbate 20 (formulation stored at 5±3° C.); (2) a formulation having 10 mM sodium phosphate, pH 6.2, 5% sucrose, 40 mM NaCl, 0.03% polysorbate 20 (formulation stored at 45° C.), and formulations respectively having, in 10 mM histidine-acetate buffer (pH 6.0) with 0.01% polysorbate 20, (3) without a salt, (4) 40 mM sodium chloride; (5) 40 mM ammonium chloride; (6) 40 mM ammonium sulfate; and (7) 40 mM potassium chloride were stored at 45° C. for 7 days. Then, same as Examples 1 and 2, monomers, aggregates, and variants produced with lapse of time were analyzed through SDS-PAGE (reducing, non-reducing), SE-HPLC, and HI-HPLC analysis.

As a result of SDS-PAGE and SE-HPLC (FIG. 6) analysis, it has been observed that, when comparing to control (2), the formulation without an additional salt ingredient of the present invention (3) showed the most excellent effect of inhibiting production of impurities and aggregates.

Example 6

Evaluation of Stability Depending on Presence and Absence of Surfactant under Shaking Condition In the present example, samples were prepared as follows in order to evaluate stability for the formulation depending on the presence and absence of polysorbate 20 and sucrose concentration during shaking, wherein the liquid formulation is based on the histidine-HCl buffer and contains, as an active ingredient, aflibercept which is an anti-VEGF-Fc fusion protein.

Specifically, the final aflibercept concentration was adjusted to 40 mg/ml, and formulations having (1) 10 mM sodium phosphate, pH 6.2, 5% sucrose, 40 mM NaCl, 0.03% polysorbate 20; (2) 10 mM histidine-acetate, pH 6.0, 10% sucrose; (3) 10 mM histidine-HCl, pH 6.0, 7.5% sucrose; (4) 10 mM histidine-HCl, pH 6.0, 5% sucrose, 0.01% polysorbate 20; (5) 10 mM histidine-HCl, pH 6.0, 7.5% sucrose, 0.01% polysorbate 20; and (6) 10 mM histidine-HCl, pH 6.0, 10% sucrose, 0.01% polysorbate 20 were respectively stored at 5±3° C. or 25° C. for 7 days with shaking at 200 rpm through an orbital shaker.

The formulation described in (1) corresponded to the formulation disclosed in International Publication WO 2007/149334. The condition described in (2) was used as a control for changes in the histidine salt buffer.

As shown in SE-HPLC and HI-HPLC analysis results, it has been found that, irrespective of the presence and absence of polysorbate, the formulation stored for 7 days at 25° C. with shaking showed inhibited production of aggregates and variants compared to control (1). In SDS-PAGE (non-reducing) (FIG. 7B) and SE-HPLC results, it has been observed that, irrespective of the presence and absence of polysorbate, the formulation stored for 7 days at 25° C. with shaking showed inhibited production of aggregates and variants compared to control (1) as well. In particular, the effect of inhibiting production of protein fragments and aggregates of the formulation without polysorbate was slightly better.

Example 7

Evaluation of Optimal Polysorbate 20 Concentration for Formulation

In the present example, to identify the optimal polysorbate 20 concentration for the liquid formulation containing, as an active ingredient, aflibercept which is an anti-VEGF-Fc fusion protein, samples were prepared as follows.

Specifically, the final aflibercept concentration was adjusted to 40 mg/ml, and (1) a formulation having 10 mM sodium phosphate, pH 6.2, 5% sucrose, 40 mM NaCl, 0.03% polysorbate 20 (formulation stored at 5±3° C.); (2) a formulation having 10 mM sodium phosphate, pH 6.2, 5% sucrose, 40 mM NaCl, 0.03% polysorbate 20 (formulation stored at 45° C.), and formulations having, in 10 mM histidine-acetate buffer (pH 6.0), 10% sucrose, and polysorbate 20 of varying concentrations of (3) 0%; (4) 0.01%; (5) 0.03%; (6) 0.05%; and (7) 0.1% were stored at 45° C. for 7 days. Then, same as Examples 1 and 2, monomers, aggregates, and variants produced with lapse of time were analyzed through SDS-PAGE (reducing, non-reducing), SE-HPLC, and HI-HPLC.

Figure 8:
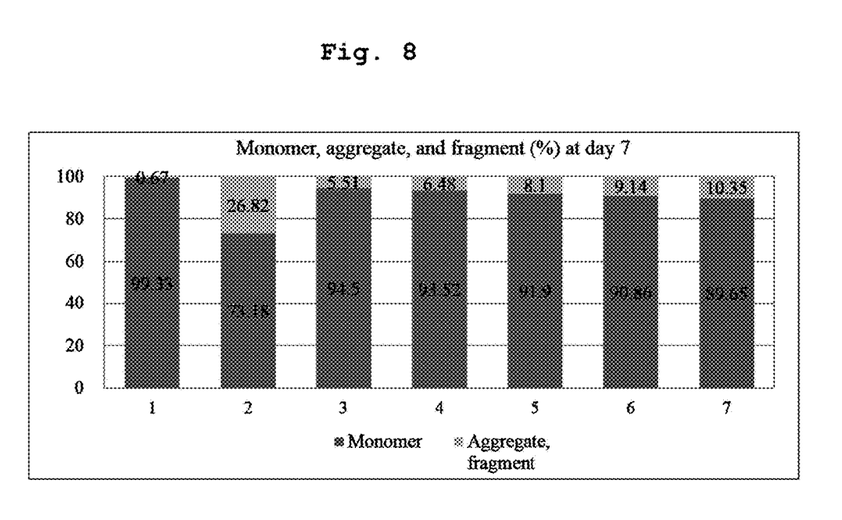
FIG. 8 is a graph measuring changes in fragment and aggregate contents (%) of a sample stored for 7 days at 45° C., wherein the sample is a formulation including various concentrations of polysorbate 20 (0%, 0.01%, 0.03%, 0.05% and 0.1%) in the histidine salt buffer including aflibercept.

In the SE-HPLC analysis results, it has been found that the formulation (3) without polysorbate 20 of the present invention and formulations (4), (5), (6) and (7) with polysorbate 20 had the superior effect of inhibiting production of aggregates and impurities than the effect of control formulation (2) (FIG. 8).

Consequently, through Examples 1 to 7, it has been found that, various conditions of liquid formulations of the present invention have greatly inhibited fragmentation and aggregation than the formulation in International Publication WO 2007/149334.

Through the formulation stability test, it has been found that the liquid formulation of the present invention has the excellent effect of inhibiting production of impurities and byproducts caused by aggregation, fragmentation and isomerization of the fusion protein having an IgG Fc domain, and thus the fusion protein can be stably stored for a long period of time and also enhanced stability can be provided under harsh conditions.

Hereinabove, particular features of the present invention are described in detail. However, it will be apparent for a person skilled in the art that the specific description is merely a preferred embodiment, and the scope of the present invention is not limited thereto. Thus, the substantial scope of the present invention will be defined by accompanying claims and equivalents thereof.

What is claimed is:

1. A liquid formulation, consisting of:
   10 to 100 mg/ml of a protein in which a soluble extracellular domain of a vascular endothelial growth factor (VEGF) receptor and an Fc domain of a human immunoglobulin G (IgG) are fused;
   a buffer consisting of a histidine salt and having pH ranging from 5.7 to 6.2; and
   a sugar selected from the group consisting of more than 6%, but not more than 10% of sucrose, trehalose, mannitol, and glucose;
   a surfactant selected from the group consisting of 0% to 0.1% of polysorbate 20 and polysorbate 80;
   wherein the soluble extracellular domain of the VEGF receptor comprises the immunoglobulin-like domain 2 of the human Flt1 VEGF receptor-1 and the immunoglobulin-like domain 3 of the human Flk1 VEGF receptor-2; and
   the histidine salt is 10 mM to 50 mM of histidine-HCl or histidine-acetate.

2. The liquid formulation of claim 1, comprising the fusion protein in an amount of 10 to 40 mg/ml.

3. A liquid formulation, consisting of:
   a buffer consisting of a histidine salt and having pH ranging from 5.7 to 6.2;
   a sugar selected from the group consisting of more than 6%, but not more than 10% of sucrose, trehalose, mannitol, and glucose;
   a surfactant selected from the group consisting of 0% to 0.1% of polysorbate 20 and polysorbate 80; and
   10 to 100 mg/ml of aflibercept;
   wherein the histidine salt is 10 mM to 50 mM of histidine-HCl or histidine-acetate.

4. The liquid formulation of claim 1, wherein the liquid formulation is suitable for intravitreal injection.

* * * * *

UNITED STATES PATENT AND TRADEMARK OFFICE
CERTIFICATE OF CORRECTION

PATENT NO. : 9,982,032 B2  
APPLICATION NO. : 15/190378  
DATED : May 29, 2018  
INVENTOR(S) : Soon Jae Park et al.

Page 1 of 1

It is certified that error appears in the above-identified patent and that said Letters Patent is hereby corrected as shown below:

In the Specification

Column 6, Lines 6-12 appear as below:
In the liquid formulation of the present invention, the sugar is any one selected from the group consisting of trehalose, sucrose, mannitol, sorbitol, glucose, lactose, xylitol, inositol, glycerol and hydroxypropyl cyclodextrin, and preferably any one selected from the group consisting of trehalose, sucrose, mannitol and glucose. The sugar concentration may be 2.5-10% (v/v).
Should be corrected to read as follows:
In the liquid formulation of the present invention, the sugar is any one selected from the group consisting of trehalose, sucrose, mannitol, sorbitol, glucose, lactose, xylitol, inositol, glycerol and hydroxypropyl cyclodextrin, and preferably any one selected from the group consisting of trehalose, sucrose, mannitol and glucose. The sugar concentration may be 2.5-10% (w/v).

Column 6, Lines 24-30 appear as below:
In the liquid formulation of the present invention, the surfactant may be used to ophthalmic drug delivery. The types of the surfactants are not limited, and include anionic surfactants, cationic surfactants, non-ionic surfactants, and zwitter-ionic surfactants, etc. The surfactant concentration may be about 0-0.3% (v/v), for example, 0% or 0.01% to 0.03%.
Should be correct to read as follows:
In the liquid formulation of the present invention, the surfactant may be used to ophthalmic drug delivery. The types of the surfactants are not limited, and include anionic surfactants, cationic surfactants, non-ionic surfactants, and zwitter-ionic surfactants, etc. The surfactant concentration may be about 0-0.3% (w/v), for example, 0% or 0.01% to 0.03%.

Signed and Sealed this  
Sixteenth Day of April, 2019

Andrei Iancu  
*Director of the United States Patent and Trademark Office*